United States Patent [19]

Popovich et al.

[11] Patent Number: 4,832,684

[45] Date of Patent: * May 23, 1989

[54] PERITONEAL MEMBRANE PLASMAPHERESIS

[76] Inventors: Robert P. Popovich, 2928 Kassarine Pass, Austin, Tex. 78704; Jack W. Moncrief, 3711 Green Trails South, Austin, Tex. 78731

[*] Notice: The portion of the term of this patent subsequent to Jun. 16, 2004 has been disclaimed.

[21] Appl. No.: 60,612

[22] Filed: Jun. 11, 1987

Related U.S. Application Data

[63] Continuation-in-part of Ser. No. 946,104, Dec. 22, 1986, Pat. No. 4,673,385, which is a continuation of Ser. No. 879,793, Jun. 13, 1986, abandoned, which is a continuation of Ser. No. 817,155, Jan. 7, 1986, abandoned, which is a continuation of Ser. No. 540,010, Oct. 7, 1983, abandoned.

[51] Int. Cl.$^4$ .............................................. A01M 1/00
[52] U.S. Cl. ........................................ 604/28; 604/29
[58] Field of Search .................... 604/28, 29, 4, 5, 6

[56] References Cited

U.S. PATENT DOCUMENTS

| | | | |
|---|---|---|---|
| Re. 31,688 | 9/1984 | Popovich | 604/6 |
| 3,825,493 | 7/1974 | Brown | 604/28 |
| 3,888,250 | 6/1975 | Hill | 604/28 |
| 4,133,891 | 1/1979 | Nolph | 604/28 |
| 4,239,041 | 12/1980 | Popovich | 604/28 |
| 4,663,166 | 5/1987 | Veech | 424/6 |
| 4,673,385 | 6/1987 | Popovich | 604/28 |
| 4,687,580 | 8/1987 | Malbrancq | 604/6 |

Primary Examiner—C. Fred Rosenbaum
Assistant Examiner—Mark O. Polutta

[57] ABSTRACT

A process to remove large molecules from the body involves infusion of a plasmate solution containing a vasodialating drug into the peritoneal cavity and subseaquent drainage on a prescribed schedule combined with intravenous or subcutaneous administration of an anticoagulant (e.g., heparin).

12 Claims, No Drawings

PERITONEAL MEMBRANE PLASMAPHERESIS

This application is a continuation-in-part of application Ser. No. 946,104, filed Dec. 22, 1986, (now U.S. Pat. No. 4,673,385), which is a continuation of Ser. No. 874,793, filed June 13, 1986, now abandoned which is a continuation of Ser. No. 817,155, now abandoned filed Jan. 7, 1986, which is a continuation of Ser. No. 540,010, now abandoned filed Oct. 7, 1983.

BACKGROUND OF THE INVENTION

The present invention relates to a method of medical treatment of a patient for diseases related to plasma proteins, and referred to as plasmapheresis.

To appreciate the nature of the present invention, a brief discussion of the makeup of blood is useful. Approximately 45% of the volume of blood is in the form of cellular components. These cellular components include red cells, also referred to as erthrocytes, white cells, also referred to as leukocytes, and platelets. Plasma makes up the remaining 55% of the volume of blood. Basically, plasma is the fluid portion of the blood which suspends the cells and comprises a solution of approximately 90% water, 7% protein and 3% of the various other organic and inorganic solutes.

In the past twenty years, a group of diseases have been identified which are mediated by circulated proteins and subgroups of proteins called antibodies. Many of these disease processes, for which the etiology has not been determined, have been classified as antibody-mediated diseases. An incomplete list of diseases which fall into this category would include: (1) systemic lupus erthematosus, (2) Guillain-Barre Syndrome, (3) myasthenia gravis, (4) polymyositis, (5) acute and chronic glomerulonephbritis, (6) Goodpasture's syndrome, (7) polyarteritis modosa, (8) thrombotic thrombocytopenic purpura, (9) Waldenstrom's macroglobulinemia, (10) schleroderma, (11) rheumatoid arthritis, (12) multiple sclerosis, (13) rheumatic fever, and (14) transplant rejection.

Manipulation of the production of proteins and, therefore, antibodies, became possible with the isolation and production of cortisone. This hormone and its synthetic derivatives are presently used to decrease the production and reaction of the harmful antibodies produced in the above-mentioned disease processes. Other non-cortisone drugs (immunosuppressants) first developed as cancer chemotherapy are also used to decrease the production of these antibodies. Both cortisone and immunosuppressive drugs have substantial risks and side-effects, but are presently used as the first line approach in the treatment of diseases related to antibody production.

In the late 1950's and early 1960's, it was discovered that mechanical removal of abnormal antibodies in certain disease processes could be beneficial. This was first used in the treatment of Waldenstrom's macroglobulinemia, a disease in which an abnormal protein of very large size (one million molecular weight) is produced. As the concentration of this abnormal protein increases, the blood becomes extremely viscous, producing a syndrome called hyperviscosity syndrome.

During this same period, many of the aforementioned disease processes were identified as being mediated by circulating proteins. Interest arose in the possible clinical effects of protein removal from whole blood, also known as plasmapheresis. Parallel with the development of the plasmapheresis concept was the development of sophisticated blood banking in which component therapy was defined (i.e., isolation of platelets and white blood cells, red blood cell separation, washing, storing and freezing). These new therapeutic modalities stimulated the development of technology to rapidly separate the plasma component of whole blood from the cellular components.

Separation of blood into a plasma fraction and a cellular component fraction is desirable for many medical reasons. For example, separation of blood into plasma fractions and cellular component fraction provides for a collection of plasma alone, with the cellular components being returned to the donor with a suitable portion of replacement fluid. This process is broadly referred to as "plasmapheresis." Thus, plasmapheresis provides for the collection of plasma from donors without the removal of the cellular components from the diseased plasma and returning the cellular components to the patient in admixture with a suitable replacement fluid, or by further fractionating the patient's plasma to remove the unwanted substances and returning a major portion of the patient's plasma with the cellular components. Finally, a plasmapheresis process can be employed for diagnostic purposes wherein plasma is separated from the cellular components and analyzed to detect disease-causing substances or conditions therein.

Heretofore, plasmapheresis has been accomplished extracorporeally primarily by removal of a quantity of blood from a patient, separating the cellular component from the plasma component and returning the cellular component to the patient. In some cases, replacement of the removed plasma is required. In a manual method of plasmapheresis, the desired amount of blood is removed by venipuncture. The cellular components are separated from the plasma component by a centrifuge. The plasma portion is manually removed from the centrifuge, and the cellular component is returned to the patient. Fresh plasma or a fluid supplement is returned to the patient along with the cellular component as a replacement for the separated plasma.

Plasmapheresis has also been conducted by a cell separator method. In this process, circulatory access to a patient is achieved. Instrumentation connected to the patient provides either continuous flow centrifugation or intermittent flow centrifugation. In continuous flow centrifugation, a quantity of blood is removed to a centrifugal element. Blood centrifugal and plasma are removed by a peristaltic pump to a collection container. From there, the cellular component of the blood and replacement fluid are returned to the patient. In intermittent flow centrifugation, a quantity of blood is removed to a centrifugal element by a blood pump. Operation of the centrifuge is intermittently discontinued to retrieve the cellular component, which is returned to the patient along with replacement fluids. The separated plasma is drained to a waste collection container.

Another method of plasmapheresis involves the use of an external membrane. Circulatory access to the patient is achieved and attachment is made to instrumentation including a pair of blood pumps and a plasma separator comprising a membrane. The blood removed from the patient is introduced to a membrane cell separator. Cellular components of the blood are rejected from the membrane with plasma being filtered through. The plasma is returned to a waste collection container. The cellular component is returned to the patient along with the replacement fluid.

In summary, plasmapheresis as it has heretofore been practiced involves taking blood from the body, and passing it into a separation device which separates the plasma from cellular aspects. Two things can happen then. One is to throw away the plasma, replace it with a substitute plasma, and reinfuse this into the body. By this procedure, it is possible to replace the plasma of the body, which is useful in a large number of disease states, mainly those which are manifested by the presence of large protein molecules in the body which have very adverse clinical effects. Alternatively, the offending molecules are removed from the plasma. Then, the same plasma is put back into the line and returned to the body. The separation can be made by means of centrifuge or by means of membrane filtration.

The present invention provides an alternative procedure for accomplishing protein removal in the treatment of a patient having a protein mediated disease.

SUMMARY OF THE INVENTION

The procedure of the present invention is referred to herein in a short-hand phrase of "Peritoneal Membrane Plasmapheresis" (PMP), and refers to protein removal from the blood vascular space through the peritoneal membrane. The phrase derives from the work "plasmapheresis" which refers to the separation of plasma from whole blood in order to remove offending substances, and from the fact that use is made of the peritoneal membrane. The peritoneal membrane is a semipermeable membrane located in the abdominal cavity. The present invention realizes that through the manipulation of the dynamics of mass transfer across the peritoneal membrane, protein molecules can be removed from the blood in a manner so as to effect plasmapheresis treatment of a patient.

PMP allows patients to perform protein removal treatment at home at considerably less expense than prior art techniques. It is a form of self care that provides a more gently protein removal without necessitating long term vascular access or rapid vascular depletion. One of the advantageous aspects is that there is provided continuous protein removal. That is, instead of rapid intermittent protein removal as heretofore done, protein removal occurs continuously.

Also, the present invention obviates the necessity to add volumes of replacement plasma with the concomitant risks associated with Acquired Immune Deficiency Syndrome (AIDS).

The method of this invention involves the infusion and drainage on a prescribed schedule of an irrigating fluid into and out of the peritoneal cavity (hereinafter referred to as "plasmate") containing a vasoactive drug combined with intravenous, subcutaneous, and/or concomitant intraperitoneal administration of an anticoagulant (e.g., heparin). The objective is to achieve removal of large protein molecules through the peritoneal cavity on a long term basis. The combined use of intravenous and/or intraperitoneal heparin administration permits continuous protein removal on a long term clinically efficacious basis by the addition of vasodilatory drugs to peritoneally infused fluid. As used herein, "administration" or "administering" includes any mechanism including, but not limited to, intravenous, subcutaneous, or oral introduction.

DETAILED DESCRIPTION OF THE INVENTION

I. Introductory Plasmapheresis Principles

The peritoneum is the largest serous membrane of the body. It lines the inside of the abdominal wall (the parietal peritoneum) and is reflected over the viscera (the visceral peritoneum). The space between the parietal and visceral portions of the membrane is called the peritoneal cavity. This is normally a potential space lubricated by serous fluid secreted by mesothelial cells which cover its free surface.

The microscopic anatomy of the peritoneum consists of five layers of fibrous and elastic connective tissue covered by mesothelial cells. Blood and lymphatic capillaries are located in the deepest layers in adults. Thus, for a substance to pass from the bloodstream into the peritoneal cavity, it must pass the capillary endothelium, the interstitium, the mesothelium and any fluid film resistances.

II. The Basic PMP Method

The basic PMP method generally involves a process of removing proteins from the blood vascular space through the peritoneal cavity. The mechanism of protein removal through the peritoneal membrane is that of mass transfer dynamics primarily involving solute convection with some diffusion. As to the primary convection mechanism, net osmotic and hydrostatic forces are at work to promote the movement of water out of plasma. The secondary diffusion mechanism is a matter of random kinetic movement of protein molecules, which attempt to evenly distribute throughout the space available. The convection mechanism is a matter of transperitoneal fluid shifts (ultrafiltration) which drag protein molecules through the membrane. An integral part of the protein removal process in accordance with the PMP method involves manipulation of the plasmate by addition of a vasoactive drug and the schedule of plasmate infusion/drainage (i.e., "exchanges"). The result is maximum clearances of large molecular weight proteins.

Generally, in the PMP method, plasmate containing a vasoactive drug and possibly an anticoagulant is infused into the peritoneal cavity. After a prescribed residence time period, the plasmate is drained and fresh plasmate is infused. Preferred vasoactive drugs include histamine phosphate, sodium nitroprusside, dipyridamole, and dibenzyline. Histamine phosphate is a diagnostic tool used for hyposensitivity therapy, pheochromacytoma and gastic secretion treatment. Sodium nitroprusside is a rapid acting, intravenous antihypertensive agent. Dipyridamole is a coronary vasodilator. These drugs may be used singly or in combination.

III. Determination of Optimum Exchange Schedule

To evaluate the removal of proteins via peritoneal membrane plasmapheresis (PMP) some basis is required to establish a plasmate exchange schedule which is equivalent to that which has been demonstrated to be effective using standard (extracorporeal) plasmapheresis methods. Conventional plasmapheresis treatment using centrifugal or external membrane methodology is highly intensive and intermittent in character. Treatments are usually applied one or more times per week over a time period usually extending from 2 to 5 hours. The patient is then disconnected from the machinery followed by a gradual build up of the toxin protein molecules within the patient.

The blood concentration of proteins is defined under any set of circumstances by the following general field equation:

$$\frac{d(VC)}{dt} = -KC + G \quad (1)$$

where:
C = toxic protein concentration level
V = protein volume of distribution
K = protein clearance rate
G = protein generation rate This equation can be solved for the protein build up between standard plasmapheresis treatments as follows.

Between treatments, K=0 and V=constant. Therefore, equation (1) reduces to:

$$V\frac{dC}{dt} = G \quad (2)$$

This equation can be solved for the protein concentration by integration between the initial concentration at the end of the previous plasmapheresis treatment, $C_0$, and the highest protein concentration level, $C_1$, immediately prior to the next plasmapheresis treatment during the time interval of $\Delta t$.

$$\int_{C_0}^{C_1} dC = \int_0^{\Delta t} \frac{G}{V} dt \quad (3)$$

This yields:

$$C_1 - C_0 = G/V \Delta t \quad (4)$$

$C_0$ can be expressed in terms of $C_1$ as follows:

$$C_0 = BC_1, \quad (5)$$

which yields:
$$C_1(1-B) = G/V\Delta t \quad (6)$$

Note that (1−B) is the degree of efficiency of the plasmapheresis treatment and varies between 0 and 1.0 (100% efficient). Substitution of $\phi$ for (1−B) yields an expression for $C_1$.

$$C_1 = \frac{G}{V} \frac{\Delta t}{\phi} \quad (7)$$

where:
$C_1$ = preplasmapheresis protein concentration level
G = protein generation rate
$\Delta t$ = time period between plasmapheresis treatments
$\phi$ = efficiency of plasmapheresis treatment This equation can be compared to a comparable equation defining the protein concentration level using PMP. Assuming the protein removal rate during PMP is essentially continuous, d(VC)/dt=0 in the general field equation. For these circumstances, equation (1) can be directly solved to yield (during PMP):

$$C = G/K \quad (8)$$

It is the high concentrations of toxic protein molecules which give rise to clinical pathology. thus, the maximum acceptable PMP protein concentration level is $C_1$ (the preplasmapheresis level standard treatment modalities). This yields:

$$C_1 = G/K_1 \quad (9)$$

where $K_1$ = PMP clearance required to maintain the protein concentration level at $C_1$.

Equations (7) and (9) are written in terms of the same value for $C_1$. Thus they can be equated to yield:

$$\frac{G}{K_1} = \frac{G}{V} \frac{\Delta t}{\phi} \quad (10)$$

Since G appears on both sides of the equation and can be cancelled, solving for $K_1$ gives:

$$K_1 = V/\Delta t \phi \quad (11)$$

The defines the PMP clearance required to achieve the same preplasmapheresis protein concentration level using conventional techniques.

PMP clearance, $K_1$, is in turn defined by the protein removal rate divided by the concentration level in the blood.

$$K_1 = \frac{V_D C_D}{tC} \quad (12)$$

where:
$V_D$ = drained plasmate volume
$C_D$ = protein concentration level in drained plasmate
t = time between PMP exchanges
C = protein concentration level in blood Again, both equations (11) and (12) are written in terms of the same value of $K_1$. Equating these and solving for $\Delta t$ yields the desired expression.

$$\Delta t = \frac{V}{V_D} \cdot \frac{C}{C_D} \cdot t \cdot \phi \quad (13)$$

which can be written as $$t = \frac{V_D C_D}{VC\phi} \Delta t \quad (14)$$

Equation (13) predicts the time between conventional plasmapheresis treatments which will yield the same maximum value of blood protein concentration level for a given set of PMP data.

For example, assume the following data was obtained for a two liter infusion of plasmate containing 2.0 mg Histamine Phosphate in a canine:
$V_D$ = 2250 ml drained plasmate
$C_D$ = 47 mg/dl total protein in drained plasmate
t = 2 hour dwell period
C = 5,800 mg/dl blood total protein level (5.8% protein)
The volume of distribution, V, can be estimated as the plasma volume which is approximately 4% of the canine weight of 18.18 Kg.

$V = 0.04 \times 18,180 = 727$ ml plasma volume

Conventional plasmapheresis treatments are approximately 80% efficient (i.e., 80% of circulating proteins are replaced by fresh plasma proteins during the treatment). Therefore, $\phi = 0.8$.

Substitution of these values into equation (13) yields:

$$t = \frac{727}{2250} \times \frac{5800}{47} \times 2 \times 0.8 = 63.8$$

or $t = 2.66$ days.

This states that if plasma proteins were continuously removed at the rate illustrated, this would be equivalent to performing a conventional plasmapheresis treatment once every 2.66 days.

IV. PMP Clinical Protocol

To prepare a patient for PMP treatment, a peritoneal catheter is surgically implanted into the peritoneal cavity. Then, postoperatively and using an antiseptic technique, access tubing is attached to the catheter. Using an aseptic technique, a container of sterile hypertonic or isotonic heparinized solution of 500-1000 ml is attached to the catheter access tubing. Irrigations are conducted two to three times daily until the effluent clears. The irrigation solution may be changed as frequently as required but usually is changed at least once daily.

To provide the fluid for infusion into the peritoneal cavity, a container of plasmate having added to it the appropriate vasoactive drug(s) and anticoagulant(s) is used. Preferably, the plasmate container is a plastic bag, and the vasoactive and anticoagulant drug agents are added to the bag by injection. The procedure for adding the vasoactive and anticoagulant drugs to the plasmate solution bag should be made in a manner that reduces contamination.

The plasmate containing the vasoactive and anticoagulant drug(s) is infused into the peritoneal cavity and allowed to remain there for the prescribed dwell time period, after which it is drained. Fresh plasmate with the vasoactive and anticoagulant drug(s) is then infused.

A modification of this protocol is to intermittently add vasoactive and anticoagulant drugs at prescribed time periods during a long dwell period. This is accomplished by draining a small volume of plasmate into an attached container at prescribed time intervals. Additional vasoactive and anticoagulant drugs are injected into the small volume of plasmate and reinfused into the peritoneal cavity. This process is repeated as often as required.

V. PMP Clinical Results

Clinical results discussed herein will be presented in terms of an equivalence index. This index represents the number of days between standard plasmapheresis treatments which would be equivalent to the protein removal rate observed on a PMP on a continuous basis (see Section III).

The effects of dwell time on the equivalence index is presented in Table I. In studies performed, 9 mg of Nitroprusside and 2 mg of Histamine Phosphate in 2 liters of 1.5% Dianeal was used with canine subjects. As shown in Table I, the equivalence index decreases dramatically with decreased dwell time. The equivalence index approaches clinical efficacy (in the range of 3.5-7 days) for dwell times less than seven hours for the medications indicated. The low equivalence index of 4.7 days for a two hour dwell period demonstrates that multiple or continuous drug infusions are desirable.

TABLE I

EFFECT OF DWELL TIME
(9 mg NP & 2 mg HP)

| Dwell Time (hours) | Equivalence Index (days) |
| --- | --- |
| 2 | 4.7 |
| 7 | 8.0 |
| 17 | 29.5 |

Multiple drug infusions can be accomplished utilizing either fresh or continuous dwelling plasmate. Studies made included the use of 2 mg of Histamine Phosphate per drug infusion. In the first case, the plasmate was drained following each two hour dwell period followed by infusion of fresh plasmate with 2 mg Histamine Phosphate. This resulted in the average equivalence index of 5.7 days. In the second case, 100 ml of plasmate was withdrawn after two hours. Two mg Histamine Phosphate was added to this solution followed by reinfusions; this was repeated twice. The same equivalence indexes were obtained, demonstrating that the same plasmate may be utilized for an extended time period with repeated or continuous drug infusions.

Technical analyses suggest that plasmate may be utilized with continuous or multiple, intermittent drug infusion until the protein level in the plasmate approaches approximately 25% of that in the blood. At this point, the concentration gradient between blood and plasmate will be reduced to ¾ of the initial value, with a decrease in the rate of protein transport. At some point (approaching 50% of equivalence) fresh plasmate needs to be utilized to maintain adequate protein removal rates.

The effect of Histamine Phosphate concentrations of 0, 2, 3, and 4 mg per 2 liter infusion are presented. The equivalence index is illustrated in each instance with several dwell periods. Table II shows that clinically acceptable equivalence indexes can be obtained with low Histamine Phosphate concentrations and short dwell times (2 hours), or with high concentrations of Histamine Phosphate (4 mg) and longer dwell times.

TABLE II

EFFECT OF
HISTAMINE PHOSPHATE CONCENTRATION

| Histamine Phosphate Concentration (mg) | Equivalence Index (days) | | |
| --- | --- | --- | --- |
| | 2 hr dwell | 7 hr dwell | 17 hr dwell |
| Control | 4.9 | 39.4 | 48.9 |
| 2.0 | | 8.0 | 29.5 |
| 3.0 | | 8.5 | 20.2 |
| 4.0 | | 4.2 | 10.2 |

The effect of Nitroprusside concentration in conjunction with Histamine Phosphate is illustrated in Table III. All exchanges include 2 mg Histamine Phosphate with two hour dwell times. It is seen that the equivalence indexes without Nitroprusside are only slightly greater than those containing 9 mg of Nitroprusside. This illustrates that Histamine Phosphate exhibits the dominant vasoactive effect under these circumstances.

TABLE III

EFFECT OF NITROPRUSSIDE CONCENTRATION
(Three exchanges with 2 mg HP every 2 hrs)

| | Equivalence Index - days | |
| --- | --- | --- |
| Exchange | Without NP | With 9 mg NP |
| 1 | 6.4 | 4.0 |

TABLE III-continued

EFFECT OF NITROPRUSSIDE CONCENTRATION
(Three exchanges with 2 mg HP every 2 hrs)

| Exchange | Equivalence Index - days | |
|---|---|---|
| | Without NP | With 9 mg NP |
| 2 | 5.1 | 5.4 |
| 3 | 5.0 | 4.8 |

The effect of Dibenzyline is illustrated in Table IV. Twenty-five mg of Dibenzyline was injected into 2,000 ml 1.5% Dianeal with a two hour dwell period. An equivalence index (EI) of 0.68 days was obtained. This is equivalent to performing a standard plasmapheresis treatment approximately daily and may be an excellent method to begin the PMP protocol with later switching to a drug with longer equivalence indexes. Dibenzyline is the most potent PMP agent presently known.

TABLE IV

EFFECT OF DIBENZYLINE

*2.0 liters 1.5 gm % Dextrose Dianeal
*2 hour dwell time
*25 mg Dibenzyline added to Dianeal
EI (control) = 120 days
EI (Dibenzyline) = 0.68 days A single PMP clinical study with humans was performed. The effects of Dypyridamole in a patient were tested. Dypyridamole 75 mg was administered orally, three times daily with four plasmate exchanges daily with a four hour dwell period. The results are presented in Table V. Equivalence index ranging from 2.8 to 12.6 days were obtained with a 6.5 day average value. This suggests that Dypyridamole may be an effective oral PMP pharmacological agent in adults as well as intraperitoneally.

TABLE V

DIPYRIDAMOLE - PATIENT

*75 mg orally three times daily
*4 hour dwell, 2.5 mg % Dianeal
Control EI = 42 days
PMP EI = 2.8 to 12.6 days
(6.5 average)

Overall, the clinical results demonstrate that PMP is a viable, clinical concept. Protein removal rates sufficiently high to be equivalent with standard external membrane and centrifuge techniques can be obtained. Specific protein removal rates can be optimized by variations in drug concentration and dwell times to conform to clinical requirements as outlined in Section III.

An alternative approach to performing the peritoneal membrane plasmapheresis method of the present invention would be for the patient to attach himself, for example during the evening hours while sleeping, to apparatus that provides fresh plasmate solution and the necessary vasoactive and anticoagulant drug infusions. The patient could maintain a residual plasmate volume during the day when awake, or could completely drain the peritoneal cavity and rely solely upon the protein removal accomplished during the evening hours.

VI. Combined Intravenous and Intraperitoneal Administration of PMP Method

Past PMP studies in our laboratories have shown an initial high level of total protein removal with the addition of vasodilatory drugs to the peritoneal solution. This transfer of proteins diminishes to control levels within 24–36 hours, in spite of continued addition of vasodilators. The ability to sustain high protein removal rates is a desired feature for optimum clinical application of PMP. Clinical application is defined as the efficacious removal of clinically important amounts of plasma protein over an extended time period. Also, our studies have demonstrated that after adaptation has occurred, addition of a second potent vasodilator only minimally increases protein losses. This indicates that the adaptation mechanism is pharmacologically independent of the vasodilator added. The adaptation mechanism also occurs when potent vasodilator other than histamine phosphate are infused as the initial drug.

The hypothesis that the adaptation was related to fibrin in the peritoneal membrane was considered. We have demonstrated that fibrinogen, a plasma protein, transfer during PMP. Tissue thromboplastin in the peritoneum may precipitate fibrin formation in the pores opened by vasoactive agents and subsequently decrease the transfer rate of proteins. We hypothesized that fibrin formation in the peritoneum could be prevented if heparin were also present in the peritoneal fluid. We had, however, previously demonstrated that the addition of heparin to the peritoneal fluid did not completely prevent the drug adaptation described above. We then hypothesized that the heparin must also be present in the plasma of the bloodstream to prevent the adaptation process. The combined route of intravenous and intraperitoneal administration proved to be the factor that led to improvements in continued protein removal with the addition of vasodilatory drugs to peritoneally infused fluid and prevented the adaptation which allows plasmapheresis to occur on a long term clinically efficacious basis.

A. PMP Intravenous Heparin Study

Purpose: To investigate the hypothesis that fibrin formation is occluding the transport of protein across the peritoneal membrane from the vascular space.

1. Surgical Implantation

A 20 kg female, canine model was selected for this study. In the operating room, Serotol 10 mls IV was given to induce anesthesia. Intubation was then achieved with a #7 mm intubation tube. A surgical prep was performed on the entire abdominal area including top mammaries to labia. Prep included shaving, surgical antiseptic scrub for 5 minutes, sterile drying and antiseptic spray. The animal was then placed in the supine position and secured to the O.R. table. Serotol 6 cc IVP was repeated. The dog was finally attached to an 02/metaphane anesthesia machine for maintenance during the surgical procedure.

Complete sterile, O. R. technique was maintained by the surgeon and technician. A sterile, adhesive barrier was placed on the abdominal area. The animal was then draped with head, foot and side drapes.

A midline incision (approximately 4–5 cm) was made at the umbilicus level through to the peritoneal cavity. The omentum and falciform ligament were both exteriorized, tied off, and excised. 3-0 chronic gut was utilized during the tie off procedure. Three layer closure was made of the peritoneum-skin area. Vicryl 2-0 was used for closure with simultaneous Neomycin gtts (1%) to each layer of closure.

Following the omentectomy, sterile gloves were changed along with the knife blade. Using the Moncrief Z track method, the skin was pulled laterally prior to incising for catheter insertion. The technician retracts on the opposite side of the table from the surgeon. The catheter is placed in the right inguinal area while the skin was retracted from the left side. Following the incision through to the peritoneum of approximately 2-3 cm, the skin is then released. Following insertion of the modified right angle Ash/Goretex catheter into the peritoneum, a stab wound was made posterior and lateral to the original incision.

The titanium adapter and sterile tubing were attached after the catheter was exited through the stab wound. The catheter was clamped distally during the final closure of the skin before adapter and tubing attachment. The peritoneal cavity was irrigated on the table with a solution of glucose 2.5% (optional) per 2 L with heparin 2000 u. Small amounts of the irrigation bag (2-400 ml) were infused at one time. Excellent flow was seen, however, the effluent was very bloody. The Travenol, U. V. system III was used for bag connections.

The animal was removed from anesthesia and extubated. The "Betty wrap" was applied around the abdomen and an Elizabethan collar and halter were attached. Irrigations were continued post-operatively until some clearing occurred. Approximately 50-100 mls of 2.5% solution with Vancomycin 50 mg and Heparin 2000 u were left in the peritoneal cavity. Talwin 30 mg IM was given for pain. The animal was placed in a shelter in the dog run.

2. Post Operative Stabilization Period
A. Initiated the day before surgery and continued for one week.
  1. Vancomycin 200 mg IV twice daily.
  2. Netromycine 40-65 mg/20 kg dog IM twice daily.
  3. Irrigations/500 mls of solution.
     a. heparin 2000 u
     b. Vancomycin 20 mg/500 ml-1000 mls twice daily
     c. for leakage: Vancomycine 125 mg IV twice daily for 3 days (after 1st week)
     d. Irrigation performed two or three times daily until effluent clears.

3. Study Period
A. Four hour dwell study (HEP)
B. Four hour dwell study (HEP 2)
C. Four hour dwell x 24 hours (HEP 3)
D. One exchange per 24 hours-increased histamine phosphate (HP) dose (HEP 4)
A. Study Period 1:
  Study Protocol:
  1. Wash out peritoneum.
  2. Infuse 1500 mls, 1.5% with HP 4 mg and heparin 1500 u. Give heparin IV 3000 u twice daily. Dwell x 4 hours and obtain sample.
  3. Infuse new bag of same solution and dwell for 3 hours at which time an additional dose of HP 4 mg is added to same bag to dwell overnight.
  4. Continue for 5 days. Samples for 4 hour dwells only.
  Discussion:
    Past PMP studies in our laboratories have shown an initial high level of protein removal with the addition of HP 4 mg to the peritoneal fluid. This protein loss diminishes to near control levels in 24-36 hours with the continued addition of HP 4 mg.

Based on the hypothesis that some sort of fibrinogen/fibrin occlusion on the vascular side of the peritoneum is preventing protein transfer, intravenous anticoagulants (heparin) were introduced simultaneously with the intraperitoneal HP. The data from consecutive 4 hour dwell periods shows the same type of declining protein removal with the continued addition of both HP and heparin.

B. Study Period 2: (Hep 2)
  Study Protocol:
  1. Same as period I except intravenous heparin dose is doubled.
  Discussion:
    Continuing with the anticoagulation hypothesis, the heparin dose was doubled. Results show a protein removal drop following the first HP dose, however, a protein increase on day 5 was a previously unseen phenomenon.

C. Study Period 3: (Hep 3)
  Study Protocol:
  1. Wash out peritoneum.
  2. Infuse 1500 mls/1.5% solution with HP 4 mg and heparin 1500 u. Make exchanges exactly 12 hours apart.
  3. Add HP 4 mg IP every 4 hours.
  4. Heparin 3000 u IV every 12 hours.
  5. Obtain samples before the addition of medication and after each exchange.
  6. Continue for 2.5 days.
  Discussion:
    The difference in this study approach was the regular infusion of HP 4 mg every 4 hours during several consecutive 24 hour periods. Laboratory results (FIG. 4) show the same desensitization type of pattern of study 1. On days 2 and 3 protein removal fell to nearcontrol levels.

D. Study Period 4: (Hep 4)
  Study Protocol:
  1. Wash out peritoneum.
  2. Infuse 1500 mls/2.5% solution with heparin 1500 u and HP 8 mg. Dwell for 5.5 hours, obtain sample and add HP 8 mg again. Dwell for 1 hour, obtain sample and add HP 8 mg. Dwell overnight and in A.M., obtain sample, then add HP 8 mg and dwell for 1 hour. Drain entire bag from abdomen, obtain sample and change bag.
  3. Repeat step 2 for 3 days.
  4. Concurrently each day, give heparin 3000 u subcutaneously, twice daily throughout the study.
  Discussion:
    The addition of subcutaneous heparin to the procedure of peritoneal plasmapheresis with 8 mg HP produces continued protein loss at a rate which is clinically applicable. The quantity of protein removed does not decrease with time.
    Substantial decreases in the serum protein concentrations include all fraction of protein, and the measurement of the protein fractions identified in the peritoneal drain volume supports the concept of PMP. Calculations of the removal rate demonstrate the clinical application of this improved procedure to treat protein mediated disease processes compared to standard extracorporeal plasmapheresis treatments.

| Protein Removal Rate with the Addition of Intravenous/Subcutaneous Heparin | | | |
|---|---|---|---|
| Total protein/serum | | | |
| start: 6,200 mg/dl | | | |
| end: 5,000 mg/dl | | | |
| | 24 hr dialysate total protein | | 24 hr drain volume |
| Day 2: | 600 mg/dl | × | 13.00 dl = 7,800 mg |
| Day 3: | 373 mg/dl | × | 15.50 dl = 6,696 mg |
| Day 4: | 647 mg/dl | × | 12.50 dl = 8,088 mg |
| | | | 41.00 dl    22,584 mg |
| Total Protein removed | | | 22.58 g/3 day = 7.52 g/day |
| Other Factors: | | | |
| Mean concentration = 550 mg/dl for 3 day period | | | |
| 860 g total plasma × 0.06% protein percent of plasma = 52 g protein | | | |
| start: 6,200 mg/dl × 8.6 dl = | | | 53.32 protein start |
| end: 5,000 mg/dl × 8.6 dl = | | | 40.00 g protein end |
| | | | 13.32 g missing |
| Generation Rate: | | | |
| 6 = 22.58 − 13.32 = 9.26 g/3 days = 3.1 g/day | | | |

One plasmapheresis treatment is generally defined in the medical community as the removal of 80% of the total plasma proteins every three to seven days. The following calculation was made to compare the improved PMP method results to the desired 80% effectiveness:

| Target Data: | | |
|---|---|---|
| (1) Animal weight | | 20 kg |
| % of plasma: body weight | | 4.3% |
| | | 860 gm |
| (2) Plasma volume | | 860 m |
| % protein in plasma | | 6% |
| | | 52 gm |
| (3) desired removal of 80% of 52 gms. = 41 gms | | |
| (4) 41 gms/3 days = 13.7 gms removed per day | | |
| (5) 41 gms/7 days = 5.8 gms removed per day | | |
| Data of this study: | | |
| Removed 7.52 g/day | | |
| Results: | | |
| Protein removal corresponds to the equivalent of one "standard" extracorporeal plasmapheresis treatment every 5 days. | | |

B. Conclusion:

The combination of intravenous/subcutaneous/intraperitoneal heparin and histamine phosphate produces sustained peritoneal protein removal. These results confirm the hypothesis that fibrinogen and other clotting factors prevent the transfer of protein from the vascular side of the peritoneum into the peritoneal solution without the addition of intravenous heparin.

Our clinical results demonstrate protein removal equivalent to one "standard" plasmapheresis treatment every 5 days which is within the range of clinical applicability "standards."

The foregoing description of the invention has been directed to particular examples and preferred techniques for purposes of explanation and illustration. It will be apparent, however, to those skilled in the art that modifications and changes may be made without departing from the essence of the invention. It is the applicants' intention in the following claims to cover all equivalent modifications and variations as fall within the scope of the invention.

What is claimed is:

1. A method of protein removal in the treatment of a patient having a protein mediated disease, comprising the steps of:
   administering an anticoagulant to the patient's bloodstream;
   infusing plasmate containing a vasoactive drug into the peritoneal cavity;
   allowing the plasmate to remain in the peritoneal cavity for a predetermined dwell time period sufficient to effect removal of circulating protein molecules from the blood vascular space of the body of substantially equivalent size and at a substantially equivalent removal rate to the protein removal achieved through extracorporeal plasmapheresis treatment; and
   draining the plasmate from the peritoneal cavity.

2. The method of claim 1 further comprising the step of:
   intermittently adding vasoactive drugs at predetermined points in time during the dwell time period.

3. The method of claim 1 further comprising the step of:
   continuously adding vasoactive drugs at predetermined points in time during the dwell time period.

4. The method of claim 1 wherein the vasoactive drug is chosen from a group consisting of:
   dipyridamole, sodium nitroprusside, histamin phosphate and dibenzyline.

5. The method of claim 1 further comprising the step of:
   infusing fresh plasmate containing a vasoactive drug into the peritoneal cavity.

6. The method of claim 1 wherein the dwell time period is determined from the equation:

$$t = \frac{V_D C_D}{V C \phi} \Delta t$$

t = dwell time for infused plasmate
where:
$\Delta t$ = time period between treatments in a conventional plasmapheresis protocol to be approximated by PMP
v = protein volume of distribution
c = toxic protein concentration level
$V_D$ = volume of plasma previously drained
$C_D$ = protein concentration level in drained patients
$\phi$ = efficiency rate 7. The method of claim 1 wherein the anticoagulant is administered intravenously.

8. The method of claim 1 wherein the anticoagulant is administered subcutaneously.

9. The method of claim 1 wherein the anticoagulant is heparin.

10. The method of claim 1 wherein the anticoagulant is administered orally.

11. The method of claim 1 further comprising the step of:
    intermittently readministering an anticoagulant to the patient's bloodstream.

12. The method of claim 1 further comprising the step of adding an anticoagulant drug to the plasmate for infusion into the peritoneal cavity.

* * * * *